(12) United States Patent
Baranton et al.

(10) Patent No.: US 9,521,951 B2
(45) Date of Patent: Dec. 20, 2016

(54) DEVICE AND METHOD FOR DETERMINING AT LEAST ONE OBJECTIVE EYE REFRACTION PARAMETER OF A SUBJECT DEPENDING ON A PLURALITY OF GAZE DIRECTIONS

(71) Applicants: Konogan Baranton, Charenton-le-Pont (FR); Fabien Divo, Charenton-le-Pont (FR); Guilhem Escalier, Charenton-le-Pont (FR); Martha Hernandez-Castaneda, Charenton-le-Pont (FR); Gildas Marin, Charenton-le-Pont (FR); Pedro Ourives, Charenton-le-Pont (FR); Benjamin Rousseau, Charenton-le-Pont (FR)

(72) Inventors: Konogan Baranton, Charenton-le-Pont (FR); Fabien Divo, Charenton-le-Pont (FR); Guilhem Escalier, Charenton-le-Pont (FR); Martha Hernandez-Castaneda, Charenton-le-Pont (FR); Gildas Marin, Charenton-le-Pont (FR); Pedro Ourives, Charenton-le-Pont (FR); Benjamin Rousseau, Charenton-le-Pont (FR)

(73) Assignee: ESSILOR INTERNATIONAL (COMPAGNIE GENERALE D'OPTIQUE), Charenton le Pont (FR)

( * ) Notice: Subject to any disclaimer, the term of this patent is extended or adjusted under 35 U.S.C. 154(b) by 47 days.

(21) Appl. No.: 14/366,954
(22) PCT Filed: Dec. 20, 2012
(86) PCT No.: PCT/FR2012/053033
§ 371 (c)(1),
(2) Date: Jun. 19, 2014
(87) PCT Pub. No.: WO2013/093363
PCT Pub. Date: Jun. 27, 2013

(65) Prior Publication Data
US 2015/0109578 A1 Apr. 23, 2015

(30) Foreign Application Priority Data
Dec. 22, 2011 (FR) ..................................... 11 04035

(51) Int. Cl.
*A61B 3/103* (2006.01)
*A61B 3/107* (2006.01)
(Continued)

(52) U.S. Cl.
CPC ............. *A61B 3/103* (2013.01); *A61B 3/0075* (2013.01); *A61B 3/0091* (2013.01); *A61B 3/107* (2013.01);
(Continued)

(58) Field of Classification Search
CPC ..... A61B 3/103; A61B 3/0075; A61B 3/0091; A61B 3/1035; A61B 3/107; A61B 3/152; A61B 3/0083; A61B 3/18; G02C 7/025
(Continued)

(56) References Cited

U.S. PATENT DOCUMENTS 1,351,220 A * 8/1920 Shigon ................... A61B 3/103
351/211
2,635,502 A 4/1953 Richards
(Continued)

FOREIGN PATENT DOCUMENTS

EP 1 882 444 1/2008

OTHER PUBLICATIONS

International Search Report dated Feb. 15, 2013, corresponding to PCT/FR2012/053033.

*Primary Examiner* — Zachary Wilkes
*Assistant Examiner* — George G King
(74) *Attorney, Agent, or Firm* — Young & Thompson

(57) ABSTRACT

Device and method for determining an objective eye refraction parameter of a subject depending on a plurality of gaze directions, the device includes elements for ophthalmologically measuring an objective eye refraction parameter of a subject, and elements of visual stimulation of variable proximity and intended to stimulate the visual accommodation of the subject for first and second proximity values. The
(Continued)

Figure 1:
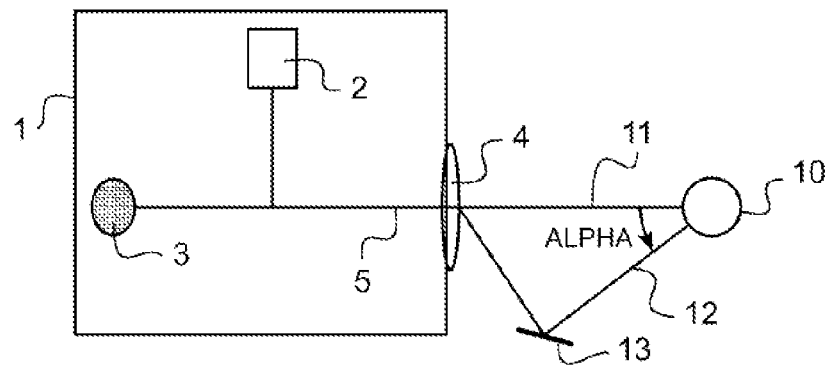

device includes opto-mechanical alignment elements for carrying out a first optical alignment of the optical axis of measurement on an eye axis in a first measuring position corresponding to a first angle of lowered viewing associated with a first proximity value to take a first measurement of an objective eye refraction parameter of the subject, and a second alignment of the optical axis of measurement on the eye axis in another measuring position corresponding to another angle of lowered viewing associated with another proximity value to take a second measurement.

15 Claims, 7 Drawing Sheets

(51) Int. Cl.
    *A61B 3/00*   (2006.01)
    *A61B 3/15*   (2006.01)
    *A61B 3/18*   (2006.01)
    *G02C 7/02*   (2006.01)
(52) U.S. Cl.
    CPC ............ *A61B 3/1035* (2013.01); *A61B 3/152* (2013.01); *A61B 3/0083* (2013.01); *A61B 3/18* (2013.01); *G02C 7/025* (2013.01)
(58) Field of Classification Search
    USPC ........................................................ 351/205
    See application file for complete search history.

(56)  References Cited

U.S. PATENT DOCUMENTS

| 2,882,789 | A | * | 4/1959 | Wilson | A61B 3/103 |
| | | | | | 351/217 |
| 4,222,639 | A | * | 9/1980 | Sheedy | A61B 3/08 |
| | | | | | 351/201 |
| 5,635,502 | A | | 6/1997 | Flynn | |
| 7,976,161 | B2 | | 7/2011 | Lemay et al. | |
| 2002/0176051 | A1 | * | 11/2002 | Saladin | A61B 3/032 |
| | | | | | 351/239 |
| 2005/0018132 | A1 | | 1/2005 | Fukuma et al. | |
| 2005/0174536 | A1 | * | 8/2005 | Hanaki | A61B 3/0091 |
| | | | | | 351/205 |
| 2010/0091241 | A1 | | 4/2010 | Lemay et al. | |
| 2011/0267576 | A1 | * | 11/2011 | Kratzer | G02C 7/02 |
| | | | | | 351/159.74 |

* cited by examiner

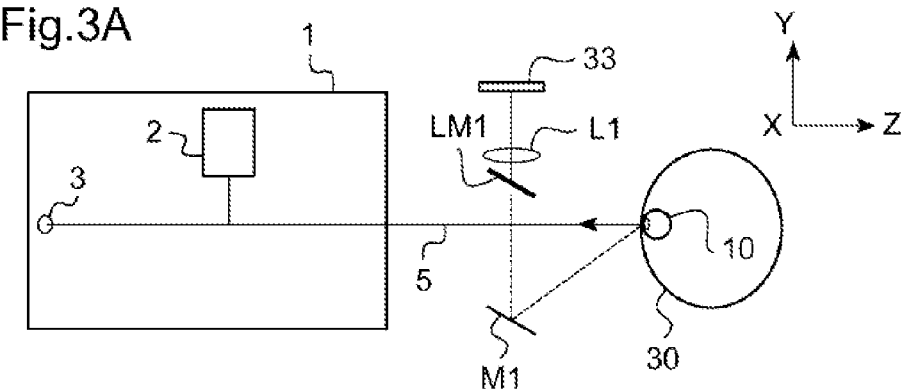
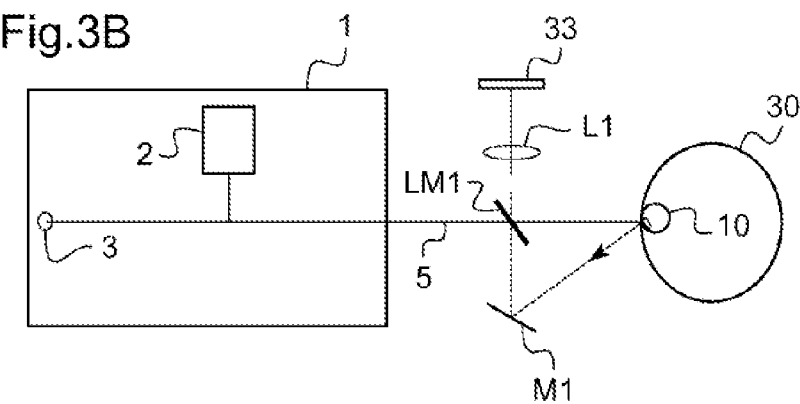
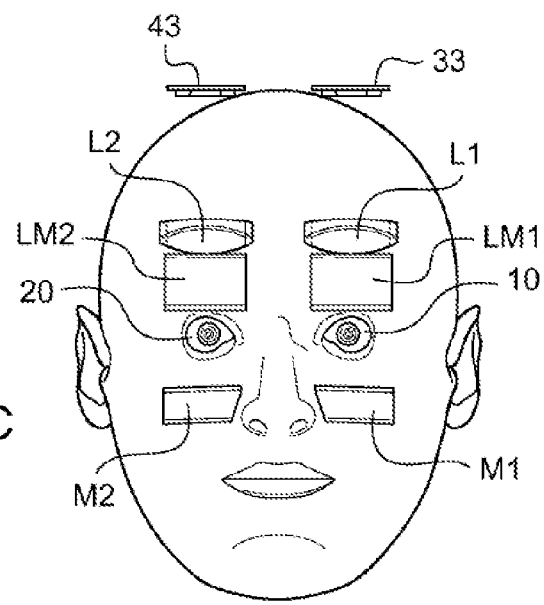

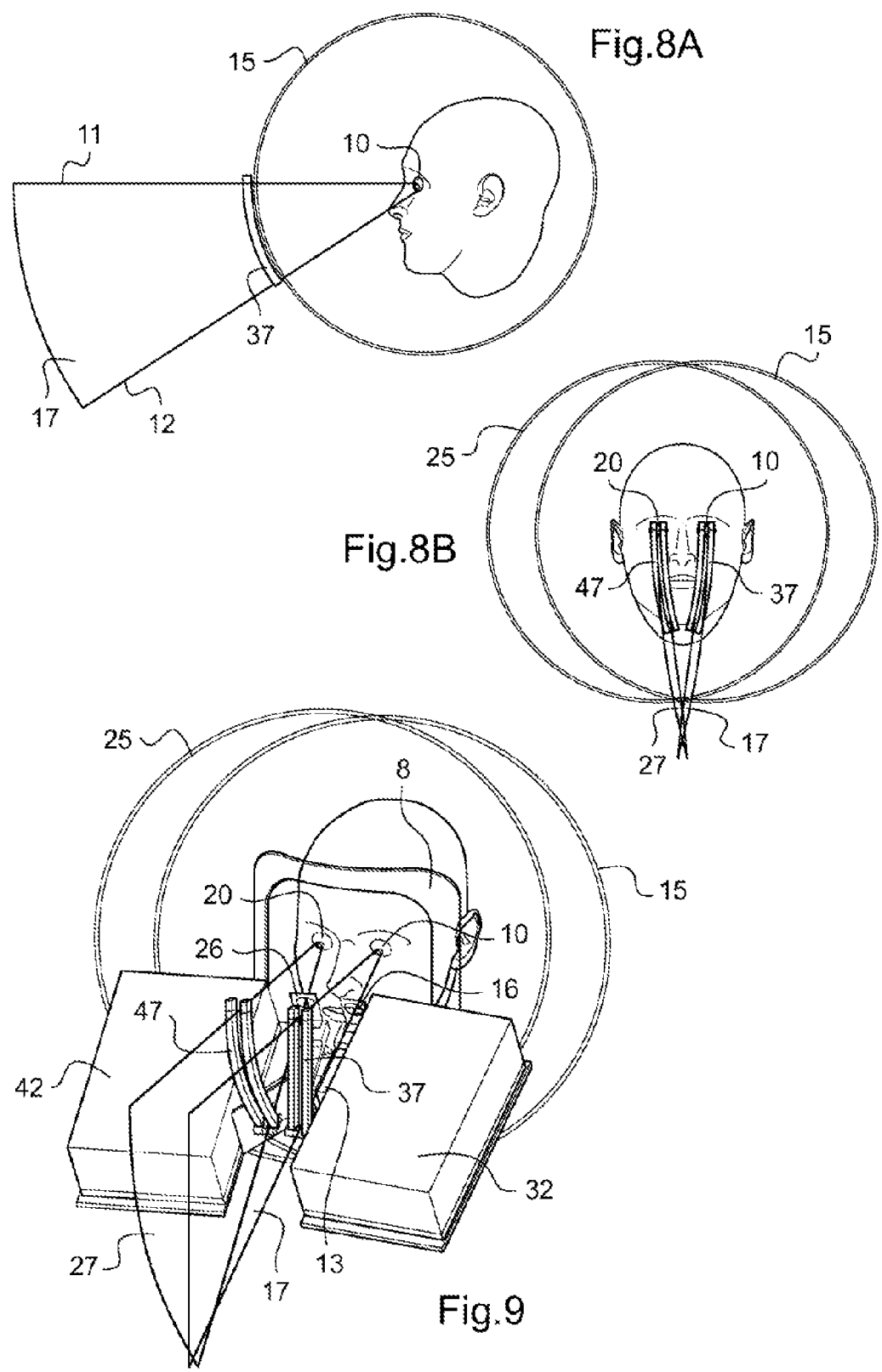

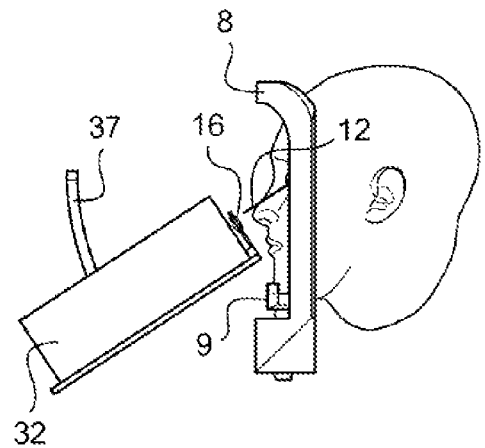
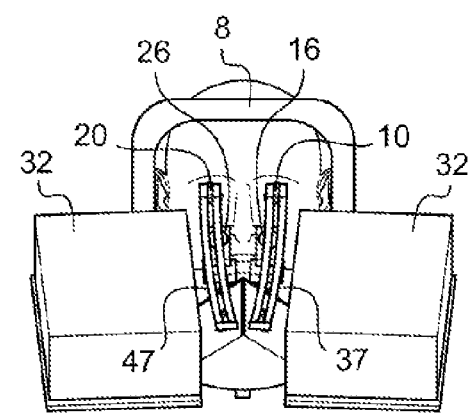
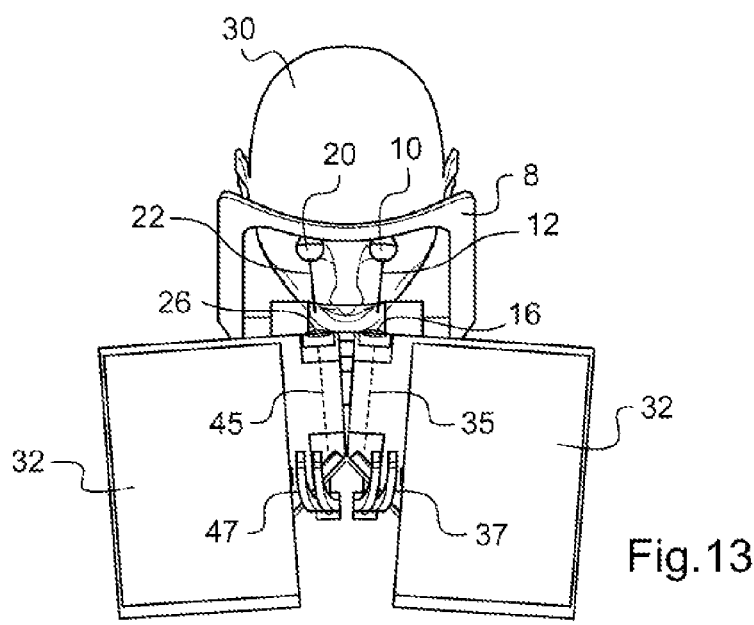

DEVICE AND METHOD FOR DETERMINING AT LEAST ONE OBJECTIVE EYE REFRACTION PARAMETER OF A SUBJECT DEPENDING ON A PLURALITY OF GAZE DIRECTIONS

TECHNICAL FIELD OF THE INVENTION

Generally, the present invention relates to the field of optometric devices and methods. More particularly, the invention relates to an optometric apparatus for determining the various values of the prescription of a lens for a pair of spectacles for progressive or multifocal visual correction, or for a pair of spectacles intended for near-vision correction (reading glasses), which values are associated with measurement of ocular refraction differentiated between a plurality of gazes and in particular a far-vision gaze and a near-vision gaze. These measurements are intended to be used for the optical design and the manufacture of the refracting faces of corrective progressive or multifocal lenses for pairs of spectacles, or for pairs of spectacles intended to correct near vision (non-prescription, reading glasses), whether it is a question of passive lenses or lenses having electronically controlled variable optical powers.

PRIOR ART

Over the last fifty odd years the market for multifocal and progressive spectacle lenses has experienced considerable growth. A multifocal lens has at least two separate corrective powers in two zones of the lens corresponding to two vision distances. A progressive lens has an optical power that varies over the surface of the lens, varying, for example in the case of correction of presbyopia, from a zone where the spherical power is low for far vision (FV) to a zone where the spherical power is higher for near vision (NV). A progressive lens generally provides an average correction for a vision distance intermediate between the far-vision and the near-vision distances. Multifocal or progressive spectacle lenses make it possible for the wearer to benefit from an optical power correction that is adapted to various vision distances without changing spectacles. In order to determine the parameters of multifocal lenses or of progressive lenses, monocular or binocular optometric apparatuses are used to measure the near-vision and far-vision optical correction to apply, the sight axis of the gaze remaining horizontal for these measurements whatever the distance focused on. Optometric apparatuses employing the measurement of the refraction of a light beam from an eye thus allow FV/NV differentiated power correction (or sphere) to be measured, i.e. the near-vision and far-vision corrections to be applied to the measured eye. Progressive or multifocal lenses are not only able to correct an optical power error but also other visual defects, in particular astigmatism. Based on the same ocular refraction measuring principle, most optometric apparatuses allow astigmatism correcting parameters (cylinder and axis) and/or higher-order aberration correcting parameters, to be measured (see standard ISO 24157:2008, which specifies standardized methods allowing aberrations in the human eye to be reported).

Currently, FV/NV differentiated ocular refraction measurements are only carried out manually. An optometrist uses a test lens to determine the various values of the prescription of the lenses.

In conventional optometric apparatuses, an optical system inserted on the ocular axis adapts optical power in order to modify the visual accommodation distance of a target, the sight line of the gaze remaining horizontal.

Document US 2005/0174536 describes an apparatus for examining the ocular accommodation of a subject as a function of the change in the proximity value of a target, the angle of declination of the gaze of the subject remaining constant.

Document U.S. Pat. No. 2,635,502 describes an apparatus for testing the tone of the ocular muscles of a subject under vision conditions that are independent for each of the eyes of the subject.

Current studies of (FV/NV) differentiated refraction measurements are confronted with the problem of measuring near-vision refraction while following the physiological lowering of the gaze that accompanies this near vision. The patent document EP 1 882 444 describes a method and a device for measuring the visual properties of an eye along various gaze directions, in which an aberrometer is placed on a rotatably movable holder so as to incline the measuring axis in order to align it along a lowered gaze direction. However, if it is desired to use an apparatus that is currently commercially available in a natural lowered or raised gaze direction, it is technically difficult (or even impossible in certain cases) to align the measuring channel with the natural gaze axis of the subject. This is because the head of the subject tends to collide with the measuring apparatus since the mechanical elements of existing systems, in particular the translational stages for centering, are designed to function in a horizontal plane.

Currently, there is no autorefractor or aberrometer type optometric apparatus that allows the far-vision/near-vision differentiated refraction effect to be studied while the gaze is naturally lowered.

SUBJECT OF THE INVENTION

The aim of the invention is to improve the precision of ophthalmological measurements that are differentiated as a function of the vision distance of the subject and of the declination of the gaze, in order to improve the differentiated correction provided depending on the vision conditions experienced by a person wearing progressive or multifocal spectacle lenses. In particular, it is sought to obtain measurements of astigmatism and/or of higher-order aberrations that are FV/NV differentiated.

One of the aims of the invention is to provide an optometric device and method for carrying out FV/NV differentiated ocular refraction measurements for a subject under conditions in which their gaze is naturally lowered.

The invention aims to provide an optometric device for measuring at least one vision parameter for various set vision distances and for various set vision directions. In particular, the invention aims to provide an optometric device allowing measurements to be carried out at distances and along directions that follow the natural gaze declination of the subject.

The invention also aims to provide a precise measurement of the variation in vision parameters as a function of the declination of the gaze, using objective measuring means, i.e. not requiring subjective measuring means that are complex and time-consuming to implement (for example implementing a test lens or a refractor).

In order to remedy the aforementioned drawback of the prior art, the present invention provides a device for determining at least one objective ocular refraction parameter of a subject as a function of a plurality of gaze directions of the subject, said device comprising ophthalmological means for measuring at least one objective ocular refraction parameter of a subject, said ophthalmological measuring means having at least one measuring optical axis that is/are intended to be aligned with the right ocular axis and left ocular axis of the subject, respectively, and visual stimulating means intended to stimulate the accommodation and visual convergence of the subject on a stimulating optical axis superposed on said at least one measuring optical axis, said visual stimulating means having a proximity that may be varied between a first proximity value D0 and at least one other proximity value DN.

More particularly, according to the invention a device is provided comprising opto-mechanical aligning means, said opto-mechanical aligning means being able to carry out a first optical alignment of said at least one measuring optical axis with the right and/or left ocular axis, respectively, in a first measuring position, said first measuring position corresponding to a first pair made up of a first gaze declination angle associated with a first proximity value, so as to carry out a first measurement of at least one objective ocular refraction parameter of said subject for said first gaze declination angle and proximity value pair, and said opto-mechanical aligning means being able to carry out at least one other optical alignment of said at least one measuring optical axis with the right and/or left ocular axis, respectively, in at least one other measuring position corresponding to another pair made up of another gaze declination angle associated with another proximity value, so as to carry out at least one second measurement of said at least one objective ocular refraction parameter of said subject for said at least one other gaze declination angle and proximity value pair.

The following are other nonlimiting and advantageous features of the device for determining at least one objective ocular refraction parameter of a subject as a function of a plurality of gaze directions of the subject, according to the invention:

said first gaze declination angle is an angle of zero relative to the horizontal and said first proximity value is comprised between 0 and 10 diopters;

said opto-mechanical aligning means comprise at least one semi-reflective plate and at least one shutter, said at least one semi-reflective plate being placed on said at least one measuring optical axis so as to define a first secondary measuring axis and at least one other secondary measuring axis, said at least one shutter switching so as to block said first or said at least one other secondary measuring axis, said first secondary measuring axis being intended to be aligned with an ocular axis oriented along a first gaze declination angle and said at least one other secondary measuring axis being intended to be aligned with an ocular axis oriented along another gaze declination angle; and said opto-mechanical aligning means comprise means for moving said ophthalmological measuring means and means for mechanically guiding the moving means along a preset trajectory depending on the gaze declination angle and the pupillary distance of a reference subject.

Advantageously, said mechanical guiding means comprise a first guiding rail taking the form of a portion of a first sphere and/or a second guiding rail taking the form of a portion of a second sphere, the first sphere being centered on the optical center of rotation of the measured right eye and/or the second sphere being centered on the optical center of rotation of the measured left eye of the subject, respectively.

Advantageously, the device of the invention furthermore comprises means for detecting the direction and the position of the gaze of said subject in said first measuring position P0 and in said at least one other measuring position PN, and controlling means for aligning said first optical alignment of said at least one measuring optical axis with the right and/or left ocular axis, respectively, in said first measuring position P0 and for aligning said at least one other optical alignment of said at least one measuring optical axis with the right and/or left ocular axis, respectively, in said at least one other measuring position PN.

Also advantageously, said opto-mechanical aligning means comprise means for adjusting the interpupillary distance or the left half-interpupillary distance or right half-interpupillary distance.

According to certain particular aspects:

the gaze declination angle relative to the horizontal is comprised between −30 degrees and +70 degrees;

the proximity value of said visual stimulating means is comprised between −3 and +10 diopters in proximity;

the device comprises a first preset position for said at least one first gaze declination angle and a second preset position for said at least one other gaze declination angle;

the measuring device comprises first ophthalmological means for measuring the ocular refraction of the right eye, first means for visually stimulating the right eye, second ophthalmological means for measuring the objective ocular refraction of the left eye, and second means for visually stimulating the left eye, said first and second stimulating means having a given proximity value for a given gaze declination angle; and the device comprises at least one optical system able to correct for at least one of the following refractive errors: a sphere, cylinder and axis error, and/or higher order aberrations for each measured eye.

The invention also provides a method for determining at least one objective ocular refraction parameter as a function of a plurality of gaze directions of a subject, said method comprising the following steps:

delivering a first visual stimulation for a first proximity value and along a first stimulating optical axis in the direction of the right eye and/or left eye, respectively of a subject having a first gaze declination angle, so as to stimulate the convergence and visual accommodation of the subject for a first gaze declination angle and proximity value and convergence pair;

aligning the measuring optical axis of the ophthalmological measuring means with the right ocular axis and/or with the left ocular axis of the subject, respectively, said right ocular axis and left ocular axis respectively having a first gaze declination angle for a first proximity value;

acquiring a first objective ophthalmological ocular refraction measurement for the right eye and left eye of said subject, respectively, for said first gaze declination angle and proximity value pair;

delivering a second visual stimulation for at least one other gaze declination angle and proximity value pair in the direction of the right and/or left eye, respectively, of a subject having at least one other gaze declination angle, so as to modify the stimulation of the convergence and the visual accommodation of the subject for at least one other gaze declination angle and proximity value pair;

aligning the measuring optical axis of the ophthalmological measuring means with the right ocular axis and/or the left ocular axis of a subject, respectively, said right ocular axis and left ocular axis respectively having another gaze declination angle for another proximity value;

acquiring at least one second objective ophthalmological ocular refraction measurement for the right eye and left eye of a subject, respectively, for said at least one other gaze declination angle and proximity pair; and calculating a corrected value of the objective ocular refraction of the right eye and/or left eye of a subject, respectively, as a function of the gaze declination angle of the subject and depending on said first objective ophthalmological ocular refraction measurement for said first gaze declination angle and proximity pair and on said at least one other objective ophthalmological ocular refraction measurement for said at least one other gaze declination angle and proximity pair.

According to particular and advantageous aspects of the method according to the invention:

the first objective ophthalmological ocular refraction measurement for said first gaze declination angle and proximity pair is carried out at a first time t0, and said at least one other objective ophthalmological ocular refraction measurement for said other gaze declination angle and proximity pair is carried out at another time t0+T, the times t0 and t0+T being preset;

at least one measured objective ocular refraction parameter is selected, nonlimitingly, from: sphere, cylinder, axis, higher-order aberrations, keratometry and corneal topography or a measurement of one of these parameters differentiated between two gaze declination angles; and the objective differential measurement is used as input data in the manufacturing design of a corrective progressive or multifocal lens for a pair of spectacles.

DETAILED DESCRIPTION OF AN EXAMPLE EMBODIMENT

The following description, given with regard to the appended drawings, by way of nonlimiting example, will allow what the invention consists of and how it can be carried out to be understood.

Figure 2:
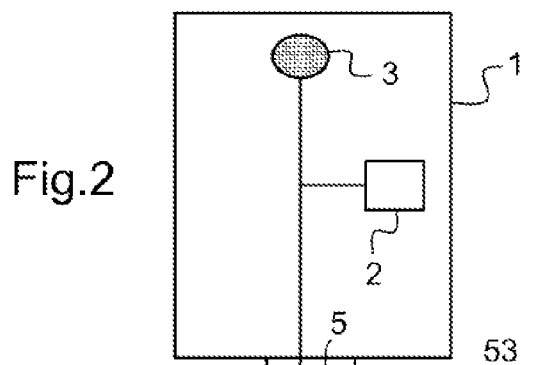
Figure 4:
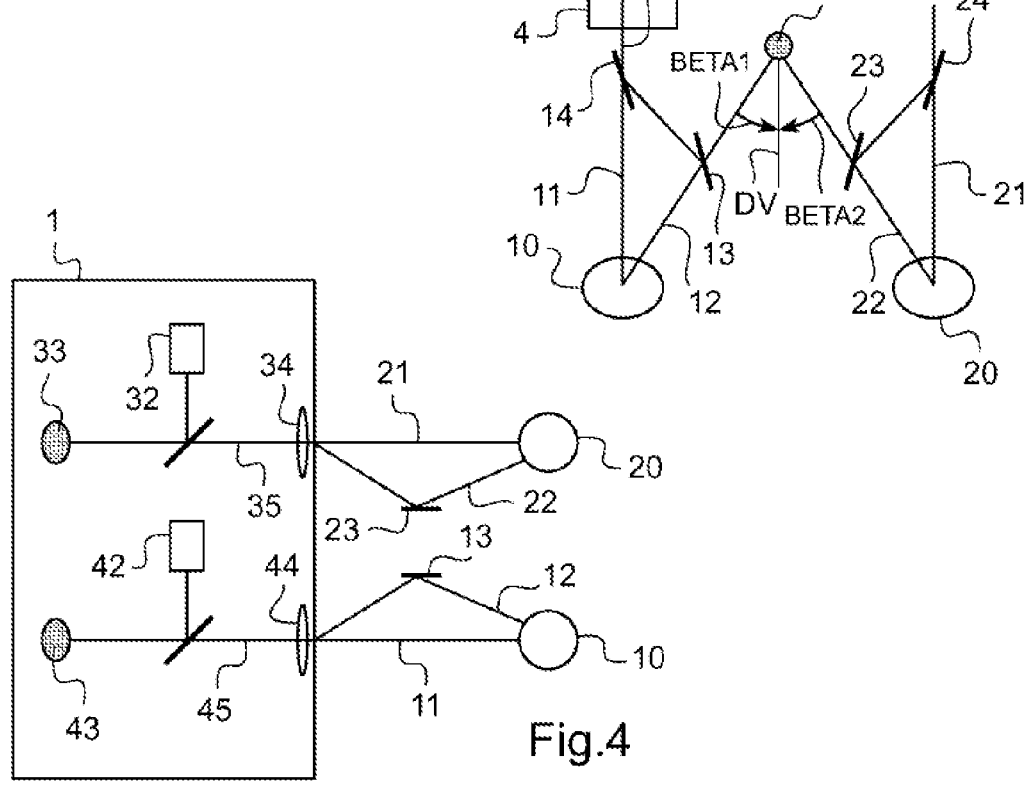
Figure 5:
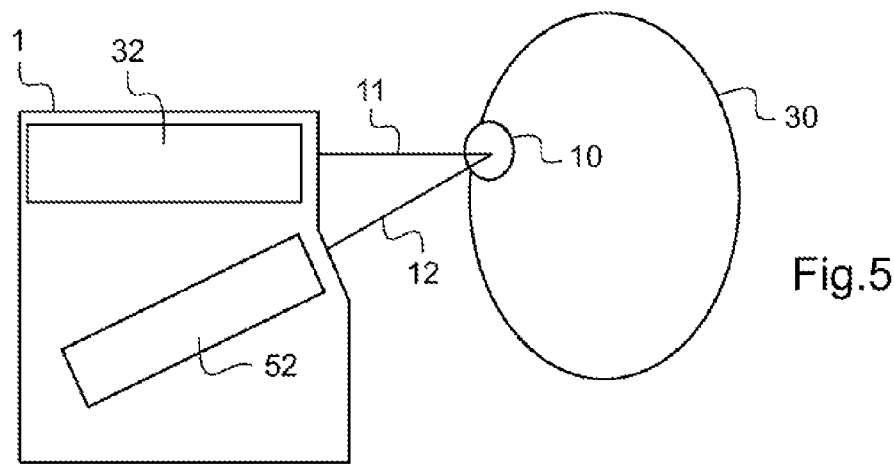
Figure 6:
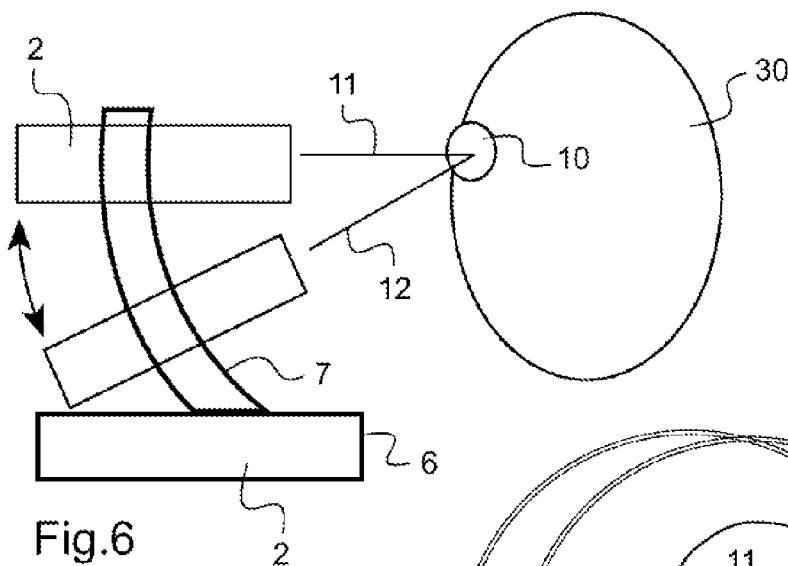
Figure 7:
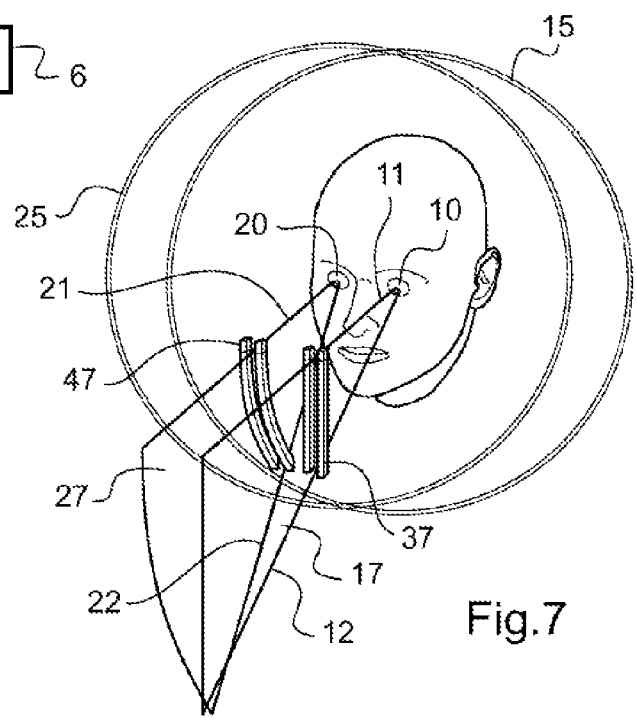
Figure 10A:
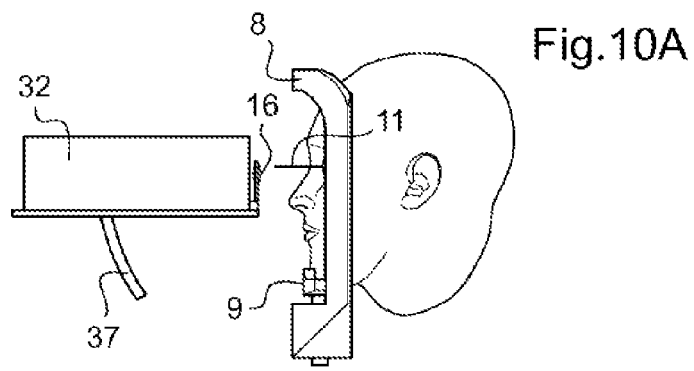
Figure 10B:
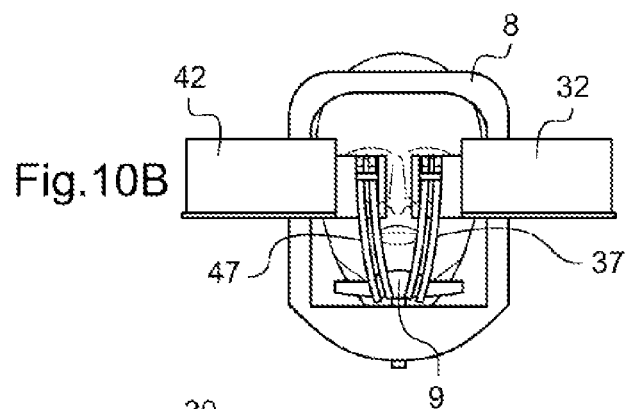
Figure 11:
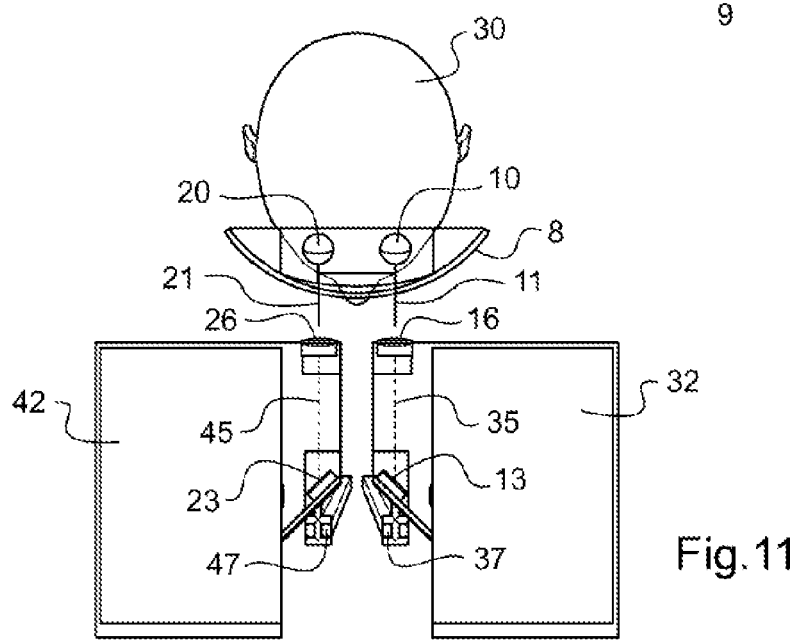

In the appended drawings:

FIG. 1 schematically shows a monocular device according to a first embodiment of the invention;

FIG. 2 shows a top view of a binocular FV/NV differentiated optometric device according to a second embodiment of the invention;

FIGS. 3A-3E schematically show an accessory for a monocular or binocular device according to one preferred embodiment of the invention;

FIG. 4 schematically shows a binocular device according to a third embodiment of the invention;

FIG. 5 schematically shows a monocular or binocular device according to a fourth embodiment of the invention;

FIG. 6 schematically shows a monocular or binocular device according to one embodiment of the invention;

FIG. 7 schematically shows a perspective view depicting the right and left ocular axes as a function of gaze declination and a guiding system for following the direction of the gaze;

FIG. 8 schematically shows a side view (FIG. 8A) and a front view (FIG. 8B) of the right and left ocular axes as a function of gaze declination and a guiding system for following the direction of the gaze;

FIG. 9 schematically shows a perspective view of a binocular device according to one embodiment of the invention;

FIGS. 10A-10B schematically show a side view (FIG. 10A) and a front view (FIG. 10B) of the device in FIG. 9 for a measurement with a zero gaze declination;

FIG. 11 schematically shows a top view of the device in FIG. 9 for a measurement with a zero gaze declination;

FIG. 12 schematically shows a side view (FIG. 12A) and a front view (FIG. 12B) of the device in FIG. 9 for a measurement with a positive gaze declination; and FIG. 13 schematically shows a top view of the device in FIG. 9 for a measurement with a positive gaze declination.

A median or sagittal plane PSAG of the head of the subject 30 is defined perpendicular to the plane of FIG. 2 and passing through the point halfway between the two eyes. In the following description, as illustrated in FIGS. 3 to 13, the wearer is considered to be seated or stood such that his/her head 30 is straight, i.e. such that the Frankfurt plane of the head of the subject is substantially horizontal. In anatomy, the Frankfurt plane is the reference plane that allows the skull to be studied. Also called the Virchow plane, it passes anteriorly through the orbital floor and posteriorly above the external auditory meatus. The wearer is also said to be in an orthostatic position, in which position he/she makes a minimum of effort.

The gaze axis or sight line DV of the wearer is defined as being located in the sagittal plane of the wearer. In the case where the wearer looks at the horizon straight in front of him/her at infinity, the sight line is a straight horizontal line DVI corresponding to the primary gaze axis. The gaze axis of the wearer is initially horizontal. During the differentiated measurement described below, the wearer is led to lower or raise his/her gaze. In the case where the wearer lowers his/her gaze, the sight line DV is a straight line located in the sagittal plane and inclined relative to a horizontal line. An angle ALPHA is defined as being the gaze declination angle relative to the horizontal. The right ocular axis is defined as being the axis passing through the object focused on by the wearer and the center of the exit pupil (i.e. the image of the real pupil produced by the cornea) of the right eye. Other definitions are possible, for example, the right ocular axis may be taken to be a straight line passing through the center of rotation of the right eye and through the center of the pupil of the right eye or even to be the axis connecting the object focused on to its corresponding image on the retina. All these definitions give approximately the same axis. Likewise, the left ocular axis is defined as being the axis passing through the object focused on by the wearer and the center of the exit pupil of the left eye. The gaze declination angle ALPHA is also defined as being the angle formed in the sagittal plane between a horizontal straight line (for example the straight line DVI) and a projection of the right or left ocular axis onto the sagittal plane. The gaze declination angle ALPHA may take positive values (case where the wearer has his/her gaze lowered, for example in a reading position) or negative values (case where the wearer has his/her gaze raised above a horizontal line).

The angle BETA defines the convergence of the gaze. More precisely, the angle BETA1 is the left convergence formed between the sight line DV and the left ocular axis of the subject. Likewise, the angle BETA2 is the right convergence formed between the sight line DV and the right ocular axis of the subject. When the subject observes a target located in the sagittal plane, and when the half-pupillary distances are equal, the angle BETA1 is equal to −BETA2.

The so-called "far-vision position" corresponds to the wearer focusing on an object located at infinity in front of them, the sight line being horizontal. Since the image of the object is located at infinity, the ideal convergence angle of the two eyes is theoretically zero. Far vision is therefore associated with proximity parameters of zero (0 diopters) and a gaze declination angle of zero (ALPHA=0). As a result of the proximity, the effective convergence angle is generally zero for far vision (BETA1=BETA2=0). Nevertheless, if the subject has a convergence error (non-zero effective convergence) it is possible to correct for it, if this is judged to be necessary, using appropriate means such as a correcting prism for example. The so-called "near-vision position" corresponds to the subject focusing on the image of a nearby object in front of them (20 to 40 cm in front of them for example), the sight line being lowered. In the near-vision position the two eyes converge towards the image of the object. Near vision is therefore associated with non-zero proximity parameters (2 to 10 diopters) and a non-zero gaze declination angle (ALPHA comprised between 20 and 70 degrees). As a result of the proximity, the convergence angle is generally non-zero for near vision (BETA1=-BETA2 comprised between 3 degrees and 20 degrees). In the same way as for the far-vision case, if the subject has a convergence error (effective BETA1 and BETA2 different in absolute value) it is possible to correct for it, if this is judged to be necessary, using appropriate means known to those skilled in the art.

These far-vision and near-vision positions correspond to the natural vision positions of a wearer of progressive or multifocal corrective spectacle lenses, said wearer merely modifying the angle of their gaze in order to pass from a far-vision position, adopted for example when driving an automobile, to a near-vision position, adopted for example when reading a paper document. An intermediate vision position (IV), intermediate in terms of proximity (1D) and gaze declination angle (10 to 30°), for example corresponds to the comfortable distance for reading a computer screen located at a distance of 1 m.

The optimal correction of a corrective multifocal or progressive lens varies not only as a function of the proximity of a target but also conjointly as a function of the declination of the gaze. Specifically, studies that have examined the kinematics of the eyes of a subject as a function of the declination of the gaze have allowed the movement of the eyes, between a natural far-vision position (gaze axis horizontal) and a natural near-vision position (gaze axis lowered, for example in order to read a paper document) to be studied. The two eyes are observed not only to converge, which results in a change in the interpupillary distance, but also, nonlimitingly, each eye is observed to rotate about its ocular axis, the pressure of the lower eyelid on the cornea is observed to increase, and the lens is observed to decenter with the accommodation. It follows that the orientation of the physiological astigmatism axis of an eye and the value of the associated astigmatism vary when the eye passes from a natural far-vision position to a natural near-vision position. However, this variation in astigmatism between the near-vision and far-vision positions is generally not taken into account when parameterizing a corrective multifocal lens or a corrective progressive lens. More generally, it would be desirable to be able to measure ocular correction parameters (sphere, cylinder, axis, higher-order aberrations, keratometry, corneal topography, etc.) with precision as a function of the proximity of the target and as a function of the declination of the gaze, in order to be able to correct vision as a function of the natural position of the eye.

Various embodiments of the device of the invention will now be described, which embodiments allow measurement parameters to be controlled in order to pass from a far-vision measurement to a vision measurement at a smaller distance (a NV distance, inter-alia).

Device

FIG. 1 shows a side view of a monocular far-vision/near-vision differentiated optometric device according to a first embodiment of the invention. The optometric device 1 comprises an ocular refraction-based measuring system 2 and a variable proximity target 3 for stimulating far-vision and near-vision accommodation by the subject. The measuring system 2 emits a light beam along an optical axis 5 in the direction of the eye 10 of the subject to be measured, and collects the light beam refracted from the eye along the same optical axis 5. The target 3 emits a light beam along an axis collinear with the measuring optical axis 5. The FV/NV differentiated measuring device furthermore comprises an optical system (not shown) on the optical path of the target 3, for modifying the proximity value of the target relative to the eye of a subject. For this purpose, a variable power optical system is advantageously used to modify the proximity of the target. The variable power system may also be used to correct far-vision ametropia while a lowered gaze, near-vision measurement is being carried out (correcting far-vision sphere and adding addition during the lowered gaze measurement), thereby allowing the subject to clearly see the target while their gaze is lowered. Alternatively, a retractable optical system may be used, the optical system being removed from the optical path in a first measuring position (a far-vision measuring position for example) and inserted on the optical path in a second measuring position (a near-vision measuring position for example). Alternatively, a so-called Badal system may be used, which system makes use of movement of the target associated with an optical system the focal point of which is coincident with the position of the pupil of the eye of the subject. Badal systems especially allow the apparent size of the image of the target to be kept constant for all the proximity values used.

The ocular refraction-based optometric device also comprises an entrance/exit pupil 4. The differentiated measuring device furthermore comprises a mirror-based optical system 13 for modifying the direction of the measuring optical axis, so as to change the gaze declination angle when the proximity of the target is changed. A shutter or a switchable mirror allows the measuring optical axis 5 to be aligned with a first direction or with another direction, only one measuring direction being active at any given time. The eye 10 of a subject, for which it is sought to measure differentiated vision parameters, is also shown in FIG. 1. In a far-vision first position P0 of the measuring apparatus, the subject looks straight ahead. The first proximity value D0 of the target is for example set to 0 diopters. The ocular axis 11 of the eye 10 is then horizontal. In this first position P0, the optical axis 5 of the measuring apparatus is aligned with the far-vision ocular axis 11. A video camera may for example be used to image the pupil of the eye and align the optical axis of the measuring apparatus with the ocular axis in question. Thus, in the far-vision first measuring position P0 it is possible to measure ocular refraction from the eye 10 for the first proximity value D0 of the target and for a gaze declination angle of zero. In a near-vision second position P1 of the measuring apparatus the proximity value D1 of the target is adjusted to a second proximity value, for example of 2.5 diopters, so as to stimulate near-vision accommodation by the eye. Simultaneously, the shutter located external to the measuring apparatus 1 is switched in order to draw the gaze of the subject downward, and optionally to stimulate convergence of the gaze, the near-vision ocular axis 12 in this position being aligned with the measuring and stimulating optical axis by way of the mirror-based optical system 13. The mirror-based optical system 13 and the shutter allow the measuring optical axis to be switched between a first position in which it is aligned along the horizontal far-vision axis 11 and a second position in which it is aligned along the lowered near-vision axis 12. Any optical system capable of switching the measuring optical axis between two positions may be used. In the second position P1, the subject looks at the target 3, the image of which is at a second proximity value D1, along a gaze declination direction that is inclined at a preset angle ALPHA, and optionally with a gaze convergence angle BETA. Analogously, in this second position P1, the optical axis 5 of the measuring apparatus is aligned with the near-vision ocular axis 12. Thus, in the near-vision second measuring position P1 it is possible to measure ocular refraction from the eye 10 for a second proximity value of the target and for a gaze declination angle that is preferably comprised between 20 and 36 degrees. Thus, a first ocular refraction measurement is obtained for a first set of proximity values and gaze declination angle (for example D0=0 diopters, ALPHA=0 degrees) and a second ocular refraction measurement is obtained for a second set of proximity values and gaze declination angle (for example D1=2.5 diopters, ALPHA=36 degrees). Based on these measurements, a computer is used to deduce a measurement of FV/NV differentiated ocular refraction as a function of the declination of the gaze for one eye.

FIG. 2 shows a top view of a binocular far-vision/near-vision differentiated optometric device according to a second embodiment of the invention. The optometric device 1 comprises a monocular refraction-based measuring system 2 having an entrance/exit pupil 4, and a target 3 for stimulating monocular visual accommodation. The measuring system 2 emits a light beam along an optical axis 5 in the direction of an eye of the subject to be measured and collects the light beam resulting from refraction from the eye along the same optical axis 5. The measuring system 2 is mounted on a sideways moving carriage for example fitted on a translating rail (not shown in FIG. 2) that allows the measuring system to be aligned either with the ocular axis of the left eye 10 (as in FIG. 2) or with the ocular axis of the right eye 20. This moving means allows a monocular, ocular refraction measurement to be carried out for each of the two eyes in sequence, in order to deduce a binocular measurement therefrom. The direction of the measuring optical axis 5 remains constant whichever eye is measured, and whatever the direction of the sight axis of the gaze.

A pluri-directional measuring accessory is arranged external to the measuring system 2. The pluri-directional measuring accessory comprises a secondary target 53 and an optical system based on mirrors and/or semi-transparent plates. Advantageously, the secondary target 53 is arranged in the sagittal plane of the subject, and the target 53 emits an identical light beam in the direction of the left eye 10 and right eye 20 of the subject. The proximity of the secondary target 53 may be varied in order to stimulate the accommodation and convergence of both eyes simultaneously. The device in FIG. 2 furthermore includes a first optical system comprising semi-transparent plates 13 and 14 and a shutter (not shown in FIG. 2) that is switchable between a first position in which the semi-transparent plate 14 is removed from the optical pathway of the left FV ocular axis 11, and a second position in which the semi-transparent plate 14 is inserted on the optical pathway of the left NV ocular axis 12. Symmetrically, the device in FIG. 2 furthermore includes a second optical system comprising semi-transparent plates 23 and 24 and a shutter (not shown) that is switchable between a first position in which it blocks the optical pathway of the right NV ocular axis 22 and a second position in which it blocks the optical pathway of the right FV ocular axis 21. The optical system formed by the semi-transparent plates 13, 14, 23, 24 and the switchable shutters allows the direction of the stimulating and measuring optical axis to be modified so as to simultaneously change the gaze declination angle and the gaze convergence angle when the proximity of the target is changed.

In a first position P0 for measuring the far-vision ocular refraction of the left eye, the measuring system 1 in FIG. 2 is positioned so that the measuring optical axis 5 is aligned with the far-vision ocular axis 11 of the left eye, the shutter being inserted on the optical pathway of the axis 12. The proximity of the target 3 is set to infinity and the secondary target 53 is turned off. The semi-reflective plate 13 is placed on the optical path of the beam from the target 3 without deflecting the beam from the target 3, so that the beam from the target is superposed with the FV ocular axis 11 of the left eye. The second optical system comprising two semi-reflective plates 23, 24 and a shutter on the optical pathway of the right NV ocular axis 22 is placed symmetrically on the ocular axis 21 of the right eye 20 so as to stimulate the far vision of the two eyes. As described with regard to FIG. 1, in the far-vision first measuring position P0, a first ocular refraction measurement is carried out on the left eye 10 for the first proximity value of the target 3 and for a first gaze declination angle of zero. Without changing the proximity of the target 3 or the gaze declination angle, the measuring device 1 is moved sideways translationally so as to align the measuring optical axis 5 with the FV ocular axis 21 of the right eye. Likewise, in this position a first ocular refraction measurement is carried out on the right eye 20 for the first proximity value of the target 3 and for a first gaze declination angle of zero. Thus, a first binocular, ocular refraction measurement is obtained for the first proximity value D0 and the first gaze declination angle of zero.

In a second measuring position P1, the target 3 is turned off and the secondary target 53 is turned on. The proximity of the target 53 is set to a second proximity value D1. Conjointly, the two shutters are switched to free the optical pathway of the right 22 and left 12 NV ocular axes and block the optical pathway of the right 21 and left 11 FV ocular axes. Assuming that the measuring system 2 has once more been positioned facing the left eye 10, the shutters prevent the subject from looking straight ahead (FV) and draw his/her gaze toward a near-vision position. The measuring optical beam is then superposed on the target beam and on the left NV ocular axis 12. The target 53 and the semi-transparent plates 13, 23 are arranged not only to induce a convergence of the two eyes but also to cause the gaze to lower by an angle ALPHA, as shown in FIG. 1. In the second measuring position P1, the secondary target 53 induces, projected onto the plane of FIG. 2, the left NV ocular axis 12 to converge by an angle BETA1, and the right NV ocular axis 22 to converge by an angle BETA2. Conjointly, the secondary target 53 induces the gaze angle ALPHA of the left 12 and right 22 NV ocular axes to increase. In the near-vision second measuring position P1 a second ocular refraction measurement is carried out on the left eye 10 for the second proximity value D1 of the target, for a gaze declination angle ALPHA that is preferably comprised between 20 and 40 degrees. Analogously, without changing the proximity of the target 53 or the gaze declination angle, the measuring device 2 is moved translationally so as to align the measuring optical axis 5 with the NV ocular axis 22 of the right eye. Likewise, in this position a second ocular refraction measurement is carried out on the right eye 20 for the second proximity value D1 of the target 53, for the same gaze declination angle ALPHA and for a convergence angle BETA2 equal to −BETA1 (to within convergence errors). Thus, a second binocular, ocular refraction measurement is obtained for the second proximity value D1 and the second gaze declination angle ALPHA.

Figure 3D:
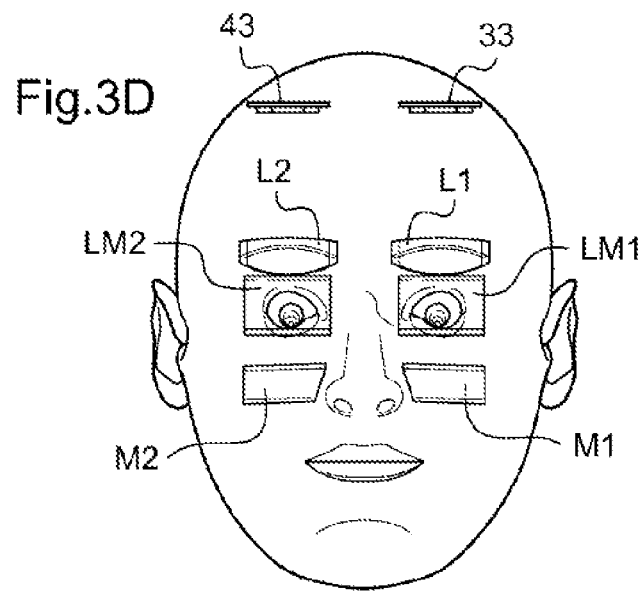
Figure 3E:
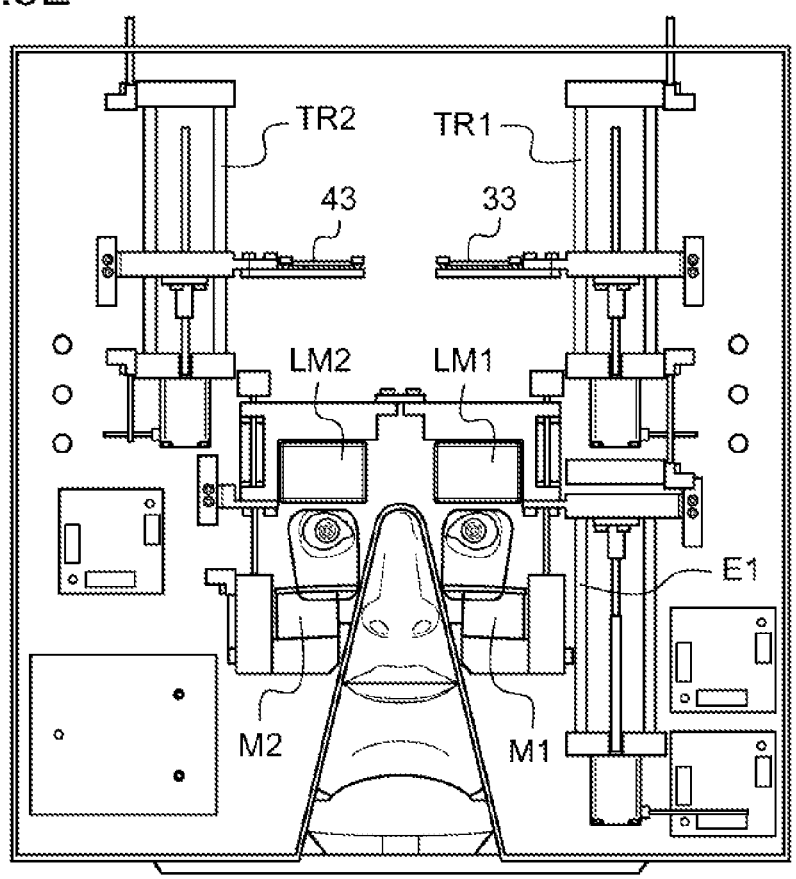

FIGS. 3A to 3E show an accessory for a monocular or binocular device according to one preferred embodiment of the invention. FIGS. 3A and 3B show the system in its entirety and FIGS. 3C and 3D show in detail the elements placed between the subject and the refraction measuring system 1. The measuring apparatus comprises an automatic refraction system 1 capable of measuring optical values of sphere, cylinder and/or axis (or S, C and A) for an eye the visual axis of which is aligned with the measuring axis 5. This automatic refraction measuring system may for example be an autorefractor or aberrometer. The automatic refraction system comprises an internal target source 3, which may be turned on or off during the refraction measurement, and the proximity of which may be adjusted. The stimulus axis defined by this target is coincident with the measuring axis 5.

The automatic refraction measuring system may be automatically or manually moved along the axes X, Y and Z. The Z-axis is used to obtain a sharply focused image of the pupil, and thus to ensure that a refraction measurement can be obtained, and that a good alignment of the sight axis with the measuring axis 5 is obtained. The X-axis is used to align the sight axis and the measuring axis horizontally, and to pass from a right eye to a left eye. The Y-axis is used to align the sight axis and the measuring axis 5 vertically.

When turned on, the target 3 serves as a target to be focused on for the measurement in a first position, otherwise it is turned off. Two other complementary targets 33 and 43 are also used and serve as targets to be focused on for the measurement in a second position. The complementary targets 33 and 43 are preferably used simultaneously, in order to promote convergence of the two eyes. These two targets 33, 43 are mounted on motorized translational systems TR1 and TR2 (see the front view in FIG. 3E), in order to allow the targets to be moved along the Y-axis, and thus their proximity to be varied. In order to optimize correction of ametropia, FV cylinder may also be taken into account. The two targets 33, 43, when they are used simultaneously, have enough properties in common to stimulate fusion, so that right and left eye see an identical target. In addition, the targets 33, 43 have a degree of mobility along the X-axis, this degree of mobility being used to correct residual convergence errors. The targets 33, 43 preferably take the form of miniature OLED display screens, or of a matrix of LEDs, or of sources that may be moved mechanically along the X-axis.

Two lenses L1 and L2, the focal points of which correspond to the position of the pupils of the right/left eyes, are placed between the eyes of the subject and the targets 33 and 43. A hot mirror LM1 (reflective in the infrared but transparent in the visible) is placed between the automatic refraction measuring system 1 and the eyes of the subject. The mirror LM1 is movable, via a mechanism E1, between two positions: a position in which the mirror LM1 is at 45° relative to the measuring axis 5, and a position in which the mirror LM1 is retracted from the measuring axis 5. Two mirrors M1 and M2 that are inclined along the X- and Z-axes are placed facing each eye so as to complete the system. The device operates in the following way:

In the first position P0, the targets 33 and 43 are turned off and the target 3 is turned on (see the side view in FIG. 3A and the front view in FIG. 3C). The proximity of the target 3 is set to 0D, the mirror LM1 is retracted from the measuring axis 5, and the measuring system 1 is moved in X, Y and Z so that the measuring axis 5 passes through the pupil of the right eye, which is focused on the target 3. This movement is carried out manually, for example by observing an image of the eye and ensuring that the pupil is correctly centered on the measuring axis 5, or automatically via automatic detection of the pupil of the eye and automatic positional control. When the X, Y, Z adjustment has finished, the ocular axis is horizontal and coincident with the measuring axis 5. The optical parameters S, C, Axis are then measured for the measured eye corresponding to this first position P0. The second eye is measured in the same way and the X, Y, Z position of each of the eyes is stored in memory.

For the second position P1, the mirrors LM1 and LM2 are translationally placed in front of the pupils of the subject, the target 3 is turned off and the targets 33 and 43 are turned on (see the side view in FIG. 3B and the front view in FIG. 3D). The mirrors M1 and M2 are positioned so that the axis of the gaze is inclined at about 30 degrees to the horizontal, and so that convergence is obtained for a proximity of about 40 cm, for an average pupillary distance of 65 mm. The targets 33 and 43 are moved translationally by the means T1 and T2 so that the image of the targets 33 and 43 generated by the lenses L1 and L2 is located at a distance of about 40 cm. If the pupillary distance is equal to 65 mm, the targets 33 and 43 are not moved translationally along the X-axis. If the pupillary distance is different from this average value, or if the proximity is changed, then the targets 33 and 43 are adjusted so that the left and right ocular axes cross at the chosen proximity value.

In practical terms, for a proximity of 40 cm and a pupillary distance larger (smaller, respectively) than 65 mm, the two targets 33 and 43 are brought closer (moved further apart, respectively) along the X-axis. For a pupillary distance of 65 mm and an increased (decreased, respectively) proximity, the two targets 33 and 43 are brought closer (moved further apart, respectively) along the X-axis. In practice, if miniature screens are used for the targets 33 and 43, the display of the targets on each of the screens is shifted horizontally by a suitable number of pixels.

Thus, the measuring system is repositioned in X, Y and Z so that the ocular axis after reflection from the mirror M1 (M2, respectively) and the mirror LM1 (LM2, respectively) is coincident with the measuring optical axis 5.

The parameters S, C, axis are then measured in this second position P1 for both eyes. In practice, the pupillary distance is determined during the measurement following the first position by memorizing the X positions for each of the eyes. Preferably, the head of the subject is supported using a head rest, against which the forehead bears, and a chin rest 9, only the eyes moving between the measuring positions P0 and P1 (see FIG. 3E).

It is also possible to use the degree of mobility of the targets 33 and 43 along the translational axes TR1 and TR2 to modify the proximity of the targets seen through the lenses L1 and L2, in order to optimize the correction of the ametropia of the subject and allow a sharp image of the targets to be obtained in the position P1.

FIG. 4 shows a top view of a binocular far-vision/near-vision differentiated optometric device according to a third embodiment of the invention. The optometric device comprises a first monocular refraction measuring system 42 having a first entrance/exit pupil 44, a first target 43 and a first measuring optical axis 45 intended to be aligned with the ocular axis of the left eye 10. The optometric device also comprises a second monocular refraction measuring system 32 having a second entrance/exit pupil 34, a second target 33 and a second measuring optical axis 35 intended to be aligned with the ocular axis of the right eye 20. The device furthermore comprises means for adjusting the left/right half-pupillary distance. Each measuring system 32, 42 operates like the device described with regard to FIG. 1. Advantageously, the device in FIG. 4 allows the first FV ocular refraction measurements to be carried out on the left eye and on the right eye simultaneously, the proximity value of the first and second target 33, 43 being set to a first value D0, the first measuring optical axis 45 being aligned with the left FV ocular axis 11 and the second measuring optical axis 35 being aligned with the right FV ocular axis 21. The device in FIG. 4 also allows the second NV ocular refraction measurements to be carried out on the left eye and on the right eye simultaneously, the proximity value of the first and second target 33, 43 being set to a second value D1, the first measuring optical axis 45 being aligned with the left NV ocular axis 12 and the second measuring optical axis 35 being aligned with the right NV optical axis 22. Thus, a binocular FV/NV differentiated measuring device is obtained without it being necessary to place a monocular apparatus in front of each eye sequentially.

FIG. 5 shows a side view of a FV/NV differentiated optometric device according to a fourth embodiment. The measuring device 32 comprises an apparatus for measuring ocular refraction and a target, which apparatus and target are aligned on one and the same optical axis, as the device 1 in FIG. 1 for example. The measuring device may be moved between two positions, indicated by the reference numbers 32 and 52 in FIG. 5. The first position 32 of the measuring system corresponds to a FV first measurement for a first proximity value and for a first gaze declination angle ALPHA1. The second position of the measuring system 52 corresponds to an NV second measurement for a second proximity value D1 and for a second gaze declination angle ALPHA. Alternatively, the differentiated measuring apparatus could comprise two measuring systems 32 and 52 in two preset positions. The system shown in FIG. 5 is either a monocular system, or a monocular system that is moved sideways to imitate a binocular system, or a binocular system comprising two monocular systems, such as the device in FIG. 3. The device in FIG. 5 allows a measurement that is differentiated between two preset positions to be taken, but it does not have an intermediate measuring position.

FIG. 6 shows a side view of a FV/NV differentiated optometric device according to another embodiment. The device in FIG. 6 comprises an ocular refraction measuring apparatus 2 and a target (not shown), which apparatus and target are aligned along one and the same optical axis, as in the device 1 in FIG. 1 for example. The measuring device 2 may be moved over a guiding system 7 of inclined shape, between a first end position and a second end position, the first end position of the measuring apparatus 2 for example corresponding to the far-vision position when the measuring axis is aligned with the far-vision ocular axis 11, and the second end position of the measuring apparatus 2 for example corresponding to the near-vision position when the measuring axis is aligned with the near-vision ocular axis 12. The measuring device in FIG. 6 also allows ocular refraction measurements to be carried out in at least one intermediate position corresponding to a third proximity value of the target and to a third gaze declination angle. The guiding system 7 is fastened to a stand 6 that is placed on a table for example. Advantageously, the guiding system ensures that the measuring system and the eye of the subject remain in optical alignment whatever the declination angle of the gaze. Also advantageously, the shape of the guiding system 7 follows a curve that reproduces the natural gaze declination and convergence movement of a reference subject.

One embodiment of a device for measuring ocular refraction differentiated as a function of proximity and gaze declination angle will now be described in detail with reference to FIGS. 7 to 13.

Advantageously, the measuring device comprises a first system 42 for measuring left-eye ocular refraction with a first target 43, and a second system 32 for measuring right-eye ocular refraction with a second target 33, as described with respect to the embodiment in FIG. 4. For the sake of legibility of FIGS. 7 and 8, these elements have not been shown, but they operate as described above. Advantageously, the measuring device comprises means for moving the first and second measuring systems 42, 32 along a preset trajectory that ensures that they always point at the optical center of rotation (OCR) of each eye.

FIG. 7 shows a guiding system comprising two sets of guiding rails 37 and 47 for guiding the first system 32, for measuring the ocular refraction of the left eye, and the second system 42, for measuring the ocular refraction of the right eye, respectively. For this purpose, the trajectory of each measuring apparatus (32, 42, respectively) is inscribed on the surface of a sphere (15, 25, respectively) the centers of which are the OCR of the left eye 10 and right eye 20, respectively. The trajectory over the guiding rails 37, 47 describes a standard movement between the FV and NV positions, taking into account the gaze declination angle, convergence and/or rotation of the eye.

FIG. 8A shows a side view of a guiding rail 37 located on a sphere 15 centered on the OCR of the left eye 10. The guiding rail ensures a circular trajectory is followed between a FV first measuring position, in which the measuring axis is aligned with the FV ocular axis 11, and a NV second measuring position, in which the measuring axis is aligned with the NV ocular axis 12. One or more intermediate measuring positions, intermediate between the FV first measuring position and the NV second measuring position, are possible. The declination of the gaze follows a surface 17 between the first and second measuring positions. FIG. 8B shows a front view of two sets of guiding rails 37 and 47. The guiding rail 37 is located on a sphere 15 centered on the OCR of the left eye 10, and the guiding rail 47 is located on a sphere 25 centered on the OCR of the right eye 20. Advantageously, the first sphere and the second sphere have the same radius. As shown in FIG. 8B, the two sets of guiding rails 37, 47 are respectively placed facing each eye in the NV position, centered on the OCR. The two trajectories 17 and 27 shift toward the nose in order to force the gaze to converge when the declination angle of the gaze is increased.

FIG. 9 schematically shows a perspective view of a binocular differentiated measuring device according to one embodiment of the invention. Two measuring systems are used: a first system 32 for measuring the ocular refraction of the left eye 10, and a second system 42 for measuring the ocular refraction of the right eye 20. The first measuring system 32 is fastened to a carriage that is able to move along the guiding rail 37, and the second measuring system 42 is fastened to a carriage that is able to move along the guiding rail 47. The first and second measuring systems 32, 42 are positioned for a FV measurement, then moved along the rails 37 and 47 downward and closer together for a NV measurement.

FIGS. 10 and 11 show the device in FIG. 9 in a far-vision (FV) first measuring position. More precisely, FIG. 10A shows a side view, FIG. 10B a front view, and FIG. 11 a top view of the device in FIG. 9 in a FV first measuring position.

The head of the user 30 is kept in a fixed position by virtue of a head rest 8 and a chin rest 9. Advantageously, the head 30 is held in a position such that the Frankfurt plane is horizontal. Alternatively, the head rest allows the inclination of the head to be adjusted to one or more other measuring positions. The first measuring system 32, which is fastened, by way of a first carriage, to the first guiding rail 37, is moved to a first position. A first optical system comprising a first deflecting mirror 13 and a first lens 16 allows the measuring optical axis of the first measuring system 32 to be deflected. Likewise, the second measuring system 42 which is fastened, by way of a second carriage, to the second guiding rail 47, is moved to a first position. A second optical system comprising a second deflecting mirror 23 and a second lens 26 allows the measuring optical axis 45 of the second measuring system 42 to be deflected. Thus, whatever their respective positions on the guiding rails 37, 47, the first and second measuring systems 32, 42 do not get in the way of each other. In the first measuring position P0, the optical axis 35 of the first measuring system 32 is aligned with the left FV ocular axis 11, and the optical axis 45 of the second measuring system 42 is aligned with the right FV ocular axis 21. In this first position, the proximity of the target is adjusted to a first proximity value D1, for example to infinity. A first measurement of the ocular refraction of the left eye 10 and of the right eye 20 may then be carried out for a first proximity value D0 of the target and for a first gaze declination angle value corresponding to the FV position.

Advantageously, the optical systems 16 and 26 are respectively able to correct a sphere, cylinder and axis error, and/or higher-order aberrations for each measured eye 10, 20 differentially as a function of gaze declination angle.

FIGS. 12 and 13 show the device in FIG. 9 in a near-vision (NV) second measuring position. More precisely, FIG. 12A shows a side view, FIG. 12B a front view, and FIG. 13 a top view of the device in FIG. 9 in a NV second measuring position.

The first carriage holds the first measuring system 32 and the first optical system (first mirror and first lens 16) and the second carriage holds the second measuring system 42 and the second optical system (second mirror and second lens 26). The first carriage is moved along the rail 37 in order to move the measuring system 32 to a NV second measuring position in which the gaze declination angle ALPHA is preferably comprised between 20 and 40°. Preferably simultaneously, the second carriage is moved along the second rail 47 in order to move the second measuring system 42 to a NV second measuring position in which the gaze declination angle ALPHA is unchanged. In this second measuring position P1, the optical axis 35 of the first measuring system 32 is aligned with the left NV ocular axis 12, and the optical axis 45 of the second measuring system 42 is aligned with the right NV ocular axis 22. In this second measuring position P1, the proximity of the two targets is adjusted to a second proximity value D1, for example to a value equal to 2.5 diopters. A second measurement of the ocular refraction of the left eye 10 and of the right eye 20 may then be carried out for a second proximity value D1 of the target and for a second gaze declination angle value corresponding to the NV position.

Those skilled in the art will understand that it is easily possible with the device in FIG. 9 to carry out at least one intermediate measurement in a position intermediate between the FV first measuring position P0 and the NV second measuring position P1, for another target proximity value/gaze declination angle pair. The device advantageously allows a preset gaze-declination and convergence trajectory to be followed, this trajectory being set by a standard model.

Method

The principle of the method is to permanently ensure a good alignment of the measuring optical axes with the ocular axes of the subject. It is also recommended for the optical axes of the visual stimulating channels to be aligned with the two preceding axes.

More generally, all possible directions of the gaze of a subject between the direction corresponding to the far-vision position and the direction corresponding to the near-vision position of a subject are of interest.

Generally, the primary position of the gaze, i.e. the measuring position in which the subject gazes straight ahead with a far-vision (FV) focus, is referred to as the initial position P0, and the associated measurement is referred to as M0.

The following parameters may be used as input data when setting the measuring conditions of the position P0:

FV Sph
FV Cyl
FV Axis
Addition
L ½ IPD
R ½ IPD

FV Sph corresponds to a far-vision power or sphere correction. The parameters FV Cyl (cylinder) and FV Axis (axis of the cylinder) define a correction for far-vision astigmatism. These values for example correspond either to an old prescription of the subject, or to the result of a subjective refraction measurement carried out beforehand by an optometrist, ophthalmologist or optician using a conventional FV method. All of these input parameters are optional and allow the target 3 and optionally the measuring module 2 to be correctly parameterized right from the start of the measurements of the subject. This makes it possible for all of the elements to be pre-positioned, and therefore makes it possible to carry out the measurements more rapidly. If these parameters are not available, they are then all measured by the apparatus.

In the initial far-vision (FV) position P0 it is possible to obtain the following measurements:

mFV Sph (measured far-vision sphere)
mFV Cyl (measured far-vision cylinder)
mFV Axis (measured far-vision axis of the cylinder)
mL ½ IPD (optional) (measured left half-pupillary distance)
mR ½ IPD (optional) (measured right half-pupillary distance)

For the other measuring directions, it is possible to set the measuring and stimulating axes relative to the right and/or left ocular axes in two ways:

1) constraints related to the progressive or multifocal corrective lenses may be used to determine the amount the gaze of the subject has to lower to pass from the position P0 to a position Pn that corresponds to a zone of a progressive glass (and therefore to a power, therefore to a proximity); or 2) natural postural parameters measured beforehand for a subject carrying out a set task (NV reading, IV consultation, etc.) may be used.

In both cases a proximity to apply to the target 3, a corresponding binocular gaze declination angle, and a correction to be made to the interpupillary distance are obtained.

The use of these three parameters allows the alignment of the visual axes to be perfectly repositioned on the measuring and stimulating axes of the system 2, 32, 42. In other words, by virtue of these various parameters the measuring and stimulating axes are adjusted so that they pass through the centers of rotation (OCRs) of the two eyes.

Once the alignment has been set, it is possible to initiate a new measurement Mn allowing the following parameters to be obtained:

mVn Sph (sphere measured in the position Pn)
mVn Cyl (cylinder measured in the position Pn)
mVn Axis (axis of the cylinder measured in the position Pn)
mLn ½ IPD (optional) (left half-pupillary distance measured in the position Pn)
mRn ½ IPD (optional) (right half-pupillary distance measured in the position Pn)

The parameters for the Vn position may be determined in the following way:

Vn Sph=mVn Sph
Vn Cyl=mVn Cyl
Vn Axis=mVn Axis

Nevertheless, it is possible to determine with greater precision the correction to be applied in the n position in the following way. Most objective refractometers do not allow the refraction of the subject to be measured with sufficient precision, or in any case with the level of precision required to provide an optimal correction of the visual defects of the subject.

Thus, to do this, the parameters FV Sph, FV Cyl, FV Axis and Add (which were obtained with precision, generally via a subjective measurement) are used as input parameters.

Next, the following formulae are applied:

$$VnSph=FVSph+(mFVSph-mVnSph)$$

$$VnCyl=FVCyl+(mFVCyl-mVnCyl)$$

$$VnAxis=FVAxis+(mFVAxis-mVnAxis)$$

Thus, at least one other measurement for the position Pn is deduced therefrom.

In order to obtain other measurements corresponding to other gaze declination angle/proximity value pairs, the measuring procedure described above may naturally be reiterated.

According to a first variant, an interpolation and/or extrapolation calculation may allow other measurements to be deduced from a set of at least two effective refraction measurements corresponding to two different pairs (of gaze declination angle and proximity value).

According to another variant, a calculation known to those skilled in the art, based on a Zernike-polynomial vector decomposition, is used to determine two components J0 and J45 representative of an astigmatism measurement (see E. A. H. Mallen et al., "Clinical evaluation of the Shin-Nippon SRW-5000 Autorefractor in adults", Ophthal. Physiol. Opt. Vol. 21, No. 2, pp. 101-107, 2001).

The overall device may be used for a binocular measurement, which ensures a good stability of the physiological accommodation and convergence parameters. However, the measurements may be carried out monocularly by forcing the sight axis of the target to reproduce the equivalent binocular position, this position providing measuring conditions that are similar but not equivalent to a binocular measurement. In both cases, the measuring and stimulating axes are aligned with the optical center or centers of rotation (OCR) of the eye or eyes.

Implementation

Preferably, the following adjustment parameters are used.

Under the conditions set by a glass, whether parameterizable or not, the proximity to be given to the target will possibly be 2.5 diopters in NV. However, it is interesting to note that this value may be modified over a range comprised between 1 and 5 diopters and adjusted so as to correspond to a measurement carried out on the subject. A gaze declination angle comprised between 0 and 40 degrees may be targeted for the component of the gaze declination angle due to the eyes alone. If only two positions are measured (FV/NV for example) declination angles of 0 and 36 degrees will preferably be chosen (or any other declination angle corresponding to variants of the progressive or multifocal corrective lens the progression length of which it is desired to configure). The inclination of the head 30 may also vary, the angle of inclination of the Frankfurt plane being comprised between −30 and 30 degrees. Thus the dynamic range of the measurement encompasses a gaze declination angular range comprised between −30 and 70 degrees.

The value of the half-pupillary distance parameter (½ IPD) may be adapted symmetrically or asymmetrically (adjusted by half-IPD) and on the basis of an exterior measurement or on the basis of a FV recalibration of the apparatus during the alignment.

The invention is particularly suitable for anyone who takes refraction-based ophthalmological measurements and who wants to provide or carry out measurements that take into account physiological declination of the head and eyes of the subject. The device of the invention may be used by an optometrist or an ophthalmologist, or even by an optician in order to determine parameters for personalizing a spectacle glass. The device and method and the invention may serve to define the means required to prescribe a progressive or multifocal corrective lens.

The invention claimed is:

1. A device for determining at least one objective ocular refraction parameter of a subject as a function of a plurality of gaze directions of the subject, said device comprising:
   an ophthalmological measurement system configured to measure at least one objective ocular refraction parameter of a subject, said ophthalmological measurement system having at least one measuring optical axis that is configured to be aligned with the right ocular axis and the left ocular axis of the subject, respectively;
   a visual stimulation system configured to stimulate the accommodation and visual convergence of the subject on at least one stimulating optical axis superposed on said at least one measuring optical axis, said visual stimulation system having a proximity configured to be varied between a first proximity value and at least one other proximity value; and
   an opto-mechanical alignment system comprising
      a moving system configured to move the ophthalmological measurement system, and
      a mechanical guiding system mechanically guiding the moving system along a preset trajectory depending on a gaze declination angle and a pupillary distance of a reference subject, the mechanical guiding system comprising one or more of a first guiding rail that is a portion of a first sphere, and a second guiding rail that is a portion of a second sphere, the first sphere being centered on the optical center of rotation of a measured right eye of the subject and/or the second sphere (15) being centered on the optical center of rotation of a measured left eye of the subject, respectively, the opto-mechanical alignment system being configured to carry out a first optical alignment of said at least one measuring optical axis with the right ocular axis and/or the left ocular axis, respectively, in a first measuring position, said first measuring position corresponding to a first pair of a first gaze declination angle associated with a first proximity value, and simultaneously at a first value of gaze convergence angle resulting from the first proximity value, to carry out a first measurement of at least one objective ocular refraction parameter of said subject for said first gaze declination angle and proximity value pair associated with the first value of gaze convergence angle, said opto-mechanical alignment system being configured to carry out at least one other optical alignment of said at least one measuring optical axis with the right ocular axis and/or the left ocular axis, respectively, in at least one other measuring position corresponding to another pair of another gaze declination angle associated with another proximity value and simultaneously at another value of gaze convergence angle resulting from the other proximity value, to carry out at least one second measurement of said at least one objective ocular refraction parameter of said subject for said at least one other gaze declination angle and proximity value pair associated with the other value of gaze convergence angle.

2. The device for determining at least one objective ocular refraction parameter as claimed in claim 1, wherein said first gaze declination angle is an angle of zero relative to the horizontal and said first proximity value is comprised between 0 and 10 diopters.

3. The device for determining at least one objective ocular refraction parameter as claimed in claim 1, wherein said opto-mechanical alignment system comprises at least one semi-reflective plate, disposed on said at least one measuring optical axis to define a first secondary measuring axis, and at least one shutter switching to block said first secondary measuring axis, said first secondary measuring axis being configured to be aligned with an ocular axis oriented along a first gaze declination angle.

4. The device for determining at least one objective ocular refraction parameter as claimed in claim 1, further comprising an automatic detecting device configured to automatically detect the direction and the position of the gaze of said subject in said first measuring position and in said at least one other measuring position, wherein the opto-mechanical alignment system is configured to carry out said first optical alignment of said at least one measuring optical axis with the right ocular axis and/or the left ocular axis, respectively, in said first measuring position, and configured to carry out said at least one other optical alignment of said at least one measuring optical axis with the right ocular axis and/or the left ocular axis, respectively, in said at least one other measuring position.

5. The device for determining at least one objective ocular refraction parameter as claimed in claim 1, wherein the gaze declination angle relative to the horizontal is comprised between −30 degrees and +70 degrees.

6. The device for determining at least one objective ocular refraction parameter as claimed in claim 1, wherein the proximity value of said visual stimulation system is comprised between −3 and +10 diopters in proximity.

7. The device for determining at least one objective ocular refraction parameter as claimed in claim 1, wherein the device has a first preset position for said at least one first gaze declination angle and a second preset position for said at least one other gaze declination angle.

8. The device for determining at least one objective ocular refraction parameter as claimed in claim 1, wherein the device comprises a first ophthalmological measurement device configured to measure the ocular refraction of the right eye, a first visual stimulation device configured to visually stimulate the right eye, a second ophthalmological measurement device configured to measure the objective ocular refraction of the left eye, and a second visual stimulation device configured to visually stimulate the left eye, wherein said first and second stimulation devices have a given proximity value for a given gaze declination angle.

9. The device for determining at least one objective ocular refraction parameter as claimed in claim 1, further comprising at least one optical system configured to correct for at least one of the following refractive errors: a sphere, cylinder and axis error, and/or higher order aberrations for each measured eye.

10. A method for determining at least one objective ocular refraction parameter as a function of a plurality of gaze directions of a subject, said method comprising:

delivering a first visual stimulation for a first proximity value and along a first stimulating optical axis in the direction of the right eye and/or the left eye, respectively, of a subject having a first gaze declination angle, to stimulate the convergence and visual accommodation of the subject for a first gaze declination angle and proximity value pair associated simultaneously with a first value of gaze convergence angle resulting from the first proximity value;

aligning the measuring optical axis of an ophthalmological measurement system with the right ocular axis and/or with the left ocular axis of a subject, respectively, said right ocular axis and left ocular axis respectively having a first gaze declination angle for a first proximity value and simultaneously the first value of gaze convergence angle;

acquiring a first objective ophthalmological ocular refraction measurement for the right eye and left eye of said subject, respectively, for said first gaze declination angle and proximity value pair associated with the first value of gaze convergence angle;

moving the ophthalmological measurement system along a mechanical guiding system comprising one or more of a first guiding rail that is a portion of a first sphere, and a second guiding rail that is a portion of a second sphere, the first sphere being centered on the optical center of rotation of a measured right eye of the subject and/or the second sphere (15) being centered on the optical center of rotation of a measured left eye of the subject, respectively, for delivering a second visual stimulation for at least one other gaze declination angle and proximity value pair in the direction of the right eye and/or the left eye, respectively, of a subject having at least one other gaze declination angle, to modify the stimulation of the convergence and of the visual accommodation of the subject for at least one other gaze declination angle and proximity value pair associated simultaneously with another value of gaze convergence angle resulting from another proximity value;

aligning the measuring optical axis of the ophthalmological measurement system with the right ocular axis and/or the left ocular axis of the subject, respectively, said right ocular axis and the left ocular axis respectively having another gaze declination angle for another proximity value and simultaneously the other value of gaze convergence angle;

acquiring at least one second objective ophthalmological ocular refraction measurement for the right eye and left eye of the subject, respectively, for said at least one other gaze declination angle and proximity pair associated with the other value of gaze convergence angle; and calculating a corrected value of the objective ocular refraction of the right eye and/or the left eye of the subject, respectively, as a function of the gaze declination angle of the subject and depending on said first objective ophthalmological ocular refraction measurement for said first gaze declination angle and proximity pair associated with the first value of gaze convergence angle and on said at least one other objective ophthalmological ocular refraction measurement for said at least one other gaze declination angle and proximity pair associated with the other value of gaze convergence angle.

11. A method for measuring the convergence kinetics of a subject, the method comprising:

the method of claim 10, in which the first objective ophthalmological ocular refraction measurement for said first gaze declination angle and proximity pair is carried out at at a first time t0, and said at least one other objective ophthalmological ocular refraction measurement for said other gaze declination angle and proximity pair is carried out at another time t0+T, the times t0 and t0+T being preset.

12. A method for measuring the convergence kinetics of a subject, the method comprising:

the method of claim 10, in which at least one measured objective ocular refraction parameter is selected from: sphere, cylinder, axis, higher-order aberrations, keratometry and corneal topography or a measurement of one of these parameters differentiated between two gaze declination angles.

13. A method for measuring the convergence kinetics of a subject, the method comprising:

the method of claim 12, in which the objective differential measurement is used as input data in the manufacturing design of a corrective progressive or multifocal lens for a pair of spectacles.

14. The device for determining at least one objective ocular refraction parameter as claimed in claim 3, wherein the device has a first preset position for said at least one first gaze declination angle and a second preset position for said at least one other gaze declination angle.

15. The device for determining at least one objective ocular refraction parameter as claimed in claim 3, wherein the device comprises a first ophthalmological measurement device configured to measure the ocular refraction of the right eye, a first visual stimulation device configured to visually stimulate the right eye, a second ophthalmological measurement device configured to measure the objective ocular refraction of the left eye, and a second visual stimulation device configured to visually stimulate the left eye, wherein said first and second stimulation devices have a given proximity value for a given gaze declination angle.

* * * * *